United States Patent [19]

Stupecky

[11] Patent Number: 5,033,312
[45] Date of Patent: Jul. 23, 1991

[54] GAS FLOW METER HOUSING

[75] Inventor: Josef Stupecky, Irvine, Calif.

[73] Assignee: Bicore Monitoring Systems, Irvine, Calif.

[21] Appl. No.: 432,040

[22] Filed: Nov. 6, 1989

[51] Int. Cl.$^5$ .......................... G01F 1/22; G01F 1/40
[52] U.S. Cl. ................................. 73/861.53; 128/725
[58] Field of Search ........... 73/861.53, 861.54, 861.55, 73/861.58, 861.61, 861.62; 128/725

[56] References Cited

U.S. PATENT DOCUMENTS

| | | | |
|---|---|---|---|
| 1,641,744 | 9/1927 | Decker | 73/861.54 |
| 1,813,100 | 7/1931 | Swindle | 73/861.62 |
| 2,941,544 | 6/1960 | Peras . | |
| 2,989,866 | 6/1961 | Widell et al. . | |
| 3,232,288 | 2/1966 | Krobath . | |
| 3,357,244 | 12/1967 | English | 73/861.54 |
| 3,910,112 | 10/1975 | Gerlach | 73/861.53 |
| 3,989,037 | 11/1976 | Franetzki . | |
| 4,006,634 | 2/1977 | Billette et al. . | |
| 4,083,245 | 4/1978 | Osborn . | |
| 4,425,804 | 1/1984 | Mount et al. | 128/725 X |
| 4,599,907 | 7/1986 | Kraus et al. . | |
| 4,688,433 | 8/1987 | Silverwater . | |

Primary Examiner—Herbert Goldstein
Attorney, Agent, or Firm—Knobbe, Martens, Olson & Bear

[57] ABSTRACT

A variable gas flow meter for obtaining a differential pressure across a membrane having a variable area orifice. The orifice is defined by a hinged flap which swings open in the direction of gas flow. The area of the orifice enlarges with increased flow. The flow meter retains the membrane in a central housing configured to prevent the accumulation of liquids, such as moisture or mucus, which enter the line. In a first, horizontal embodiment, the housing invert is continuous and flush throughout except for a negligible ridge of membrane that remains when the orifice opens. In a second, vertical embodiment, the housing allows liquids in an upper conduit section to drop downward and flow out the device into a lower conduit section through the forces of gravity and a gas flow.

18 Claims, 3 Drawing Sheets

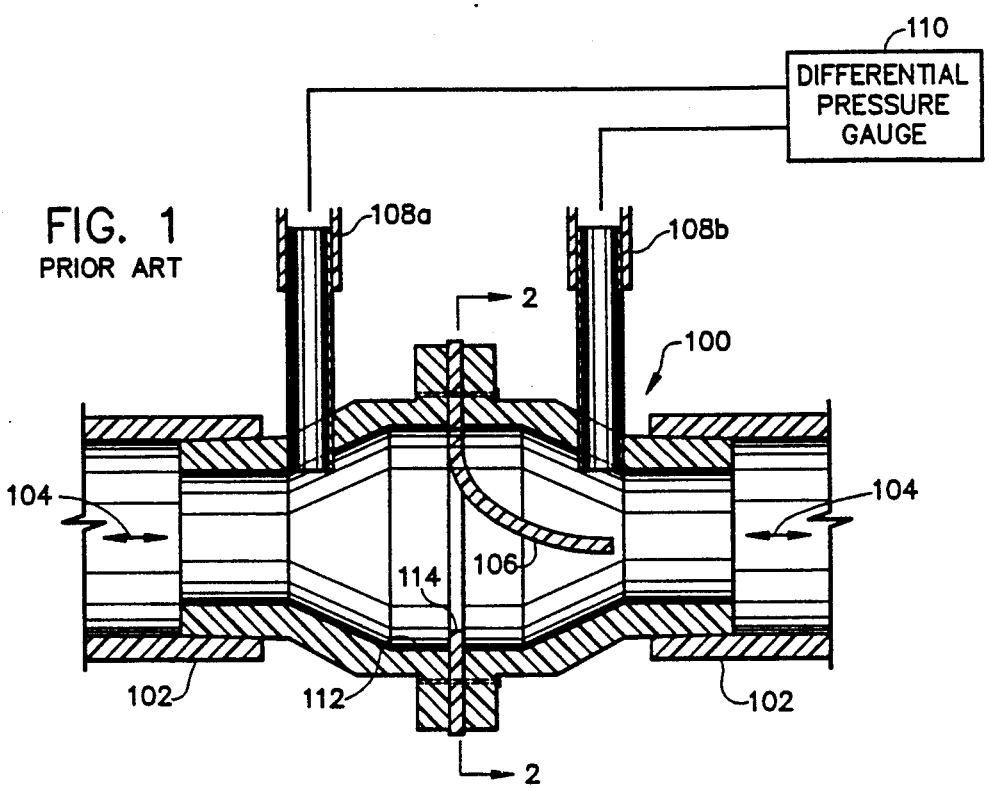
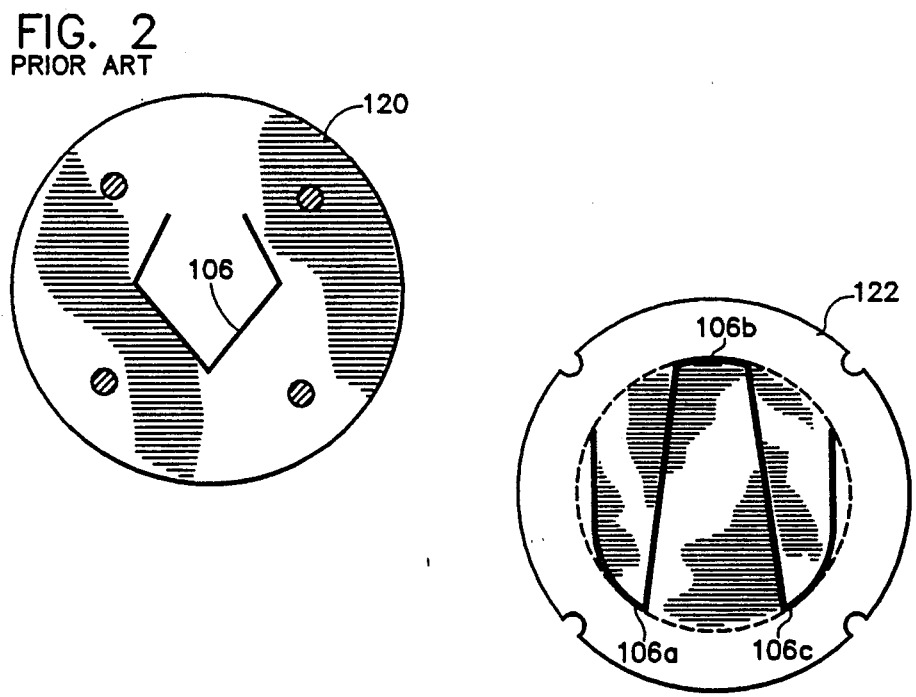

FIG. 4
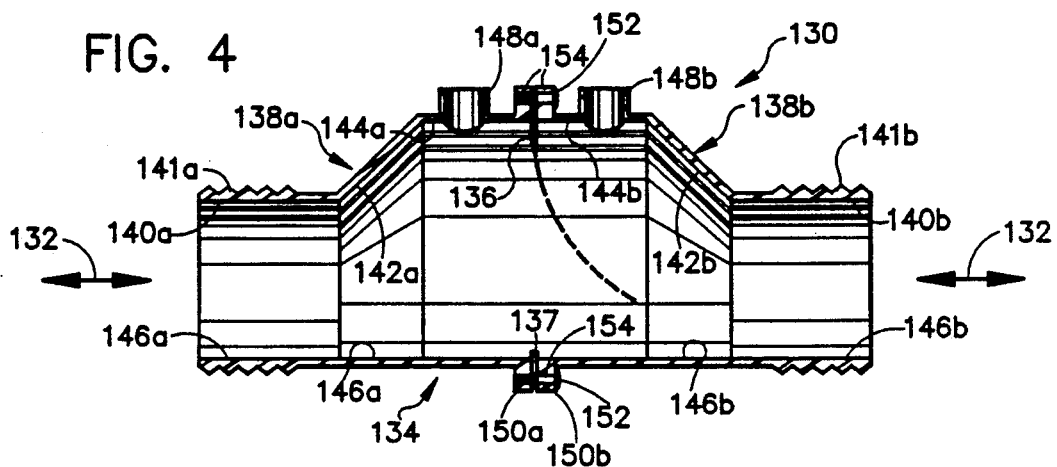
FIG. 5
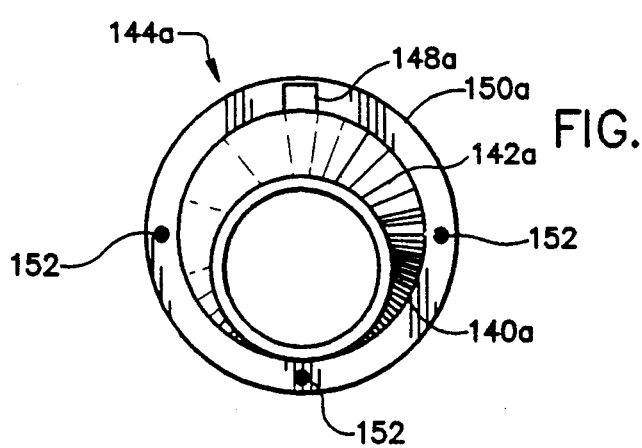
FIG. 6

GAS FLOW METER HOUSING

BACKGROUND OF THE INVENTION

1. Field of the Invention

The present invention relates to flow meters, and in particular, to the housing configuration of variable area flow meters for measuring the flow rate of a fluid such as respiratory gas in a conduit.

2. The Prior Art

Long term monitoring of respiratory air flow in critical care patients, and in patients undergoing anesthesia, is essential for correctly assessing the patient's condition, and for selecting the course of future treatment. Of course, under these circumstances, because of the necessity of very accurate and reliable measurements, it is important that the flow meter which is selected meet all of the requirements for proper operation under critical care conditions. In particular, such operating conditions require use of a lightweight flow meter having a small dead space, a broad pressure range, and an accuracy that is not affected by the presence of fluid, including mucus produced by the patient.

There are a number of different types of flow meters that are well known in the technology and which are acceptable for short term use in applications such as diagnostic pulmonary measurement. These flow meters typically comprise a housing which may be connected through a pair of sensing ports to a differential pressure transducer. The housing is connected in-line to a conduit or respiratory line which conducts gas to and from the patient, for breathing purposes.

In general, the prior devices operate by creating a resistance across a flow of gas and then using the differential pressure transducer to measure the two differing pressures communicated through the sensing ports located on either side of the resistance. This pressure differential is mathematically related to a quantity of flow by the transducer. The resistance to the gas flow is often embodied in a membrane having an orifice which is smaller than the conduit. It is well known that during laminar flow conditions the relationship between flow and pressure differential is linear. However, depending on the type of resistance employed, turbulent flow may develop locally and thus, significantly distort the linear relationship. Consequently, variable size orifices have been employed to minimize the effects of turbulent flow on the differential pressure measurements.

One example of a prior art device that incorporates a variable area orifice is described in U.S. Pat. No. 4,083,245 issued to Osborn. In the Osborn device, the orifice is created by the movement of a hinged flap which opens in the direction of flow, thus, increasing the orifice area as the flow in the conduit increases. The flap is cut out of a membrane which is installed across the opening of the interior of the device housing.

Prior devices also typically include a membrane housing such as that disclosed in the Osborn reference, whose configuration prevents the free-flow of liquids which enter the housing from the connected conduit. In particular, moisture or mucus communicated from the patient can accumulate either in a depressed well surrounding the lower portion of the membrane, or up against a membrane ridge which protrudes from the invert of the housing. The accumulated liquids are unsanitary and, moreover, prevent effective operation of the flap, thereby reducing the accuracy of the sensing device. Furthermore, removal of the accumulated liquids requires that the respiratory line be frequently shut down in order to remove the flow meter for cleaning or replacement.

In view of the above, it would be an important improvement in the art to provide a variable orifice flow meter that prevents substantially all liquids that enter the line from accumulating within the meter, and hence maintains measurement accuracy. It would be a further improvement in the art to provide a variable orifice flow meter which enhances safety to the patient by eliminating unsanitary buildup of liquids in the meter while also minimizing the downtime required to service or replace the flow meter.

SUMMARY OF THE INVENTION

The present invention provides an improved bi-directional flow meter used in respiratory systems connected to critical care patients. The invention includes a gas flow meter housing inserted in a gas flow tube, or conduit. The housing is connected in-line to the conduit by a pair of inlet/outlet ports. The housing further has a pair of differential pressure sensor ports, which may be connected to a differential pressure transducer. In this way, the invention allows a non-invasive and indirect measurement of the gas flow through the conduit by measuring a pressure difference across a resistance.

The interior of the housing contains a variable orifice membrane; that is, a resistance which dampens turbulent flow and leads to more accurate differential pressure measurements. The membrane is extended across the interior of the housing such that its primary surface area is perpendicular to the direction of gas flow, and such that it is flanked on each side by one of the two sensor ports. The housing is preferably substantially tubular in shape and, at the location where the membrane resides, has a cross-sectional diameter that is larger than that of the conduit. The larger diameter of the housing allows the use of a membrane which, because of its size, is prevented from travelling down the conduit if it should become detached from the interior wall of the housing.

The membrane is a thin, flexible sheet of elastic material, such as a stainless steel shim. In one preferred embodiment, the variable orifice is defined by three hinged leaves cut out from the membrane. Other types of variable orifice membranes may also be used, and a more detailed discussion about such membranes is available in my United States patent application entitled "VARIABLE AREA OBSTRUCTION GAS FLOW METER" filed concurrently herewith, which is hereby incorporated by this reference.

The housing is shaped to prevent the accumulation of moisture and mucus by directing such liquids out of the housing. In a first preferred embodiment of the housing, an invert of the housing lies in the same plane as an invert of the inlet/outlet ports and an invert of the conduit. An invert can be defined as the bottom of a conduit or other fluid carrying means. A central axis of the housing is defined by a line parallel to the fluid flow but non-colinear to an axis of the conduit. The housing is generally of a greater diameter than the diameter of the conduit, and fluid communication to the housing is provided by the inlet/outlet ports, which share a common central axis with the conduit. An eccentric alignment is thus formed between the housing and the conduit.

The present invention can also be described as a housing having a top and a bottom, and first and second gas inlet/outlet ports. Each such port has a diameter and the first and second ports together are adapted to direct gas horizontally through said housing in a flow path. In addition, a variable orifice membrane is disposed in the flow path between the first and second ports so as to generate a differential pressure across the membrane as a function of the flow rate of the gas through the orifice. The diameters of the first and second ports are less than the diameter of the housing at the location of the membrane, and the bottom of the housing inside the housing is substantially linear between the first and second ports so that liquid can move through said housing without substantial accumulation at the membrane.

In a second preferred embodiment, the housing is substantially "Z"-shaped so that the inlet/outlet ports are aligned with two non-colinear sections of a conduit, referred to as the upper and lower conduit sections. The axis of the housing, defined by the direction of fluid flow, is perpendicular to the axis of the inlet/outlet ports and the conduit sections. In this embodiment, the axes of the conduit sections are thus non-colinear, but they are parallel to one another and parallel to the horizontal. In addition, because the fluid flow in the housing is essentially vertical, the membrane surface is parallel to the horizontal. Any liquids condensing or otherwise being deposited in such a housing will naturally drop from the upper conduit section, connected to the patient, to the lower conduit section, connected to the respirator. When gas flows from the upper to the lower conduit section, liquids are thereby forced out of the housing by the gas flow.

Thus, the advantages of the present invention over prior art variable orifice flow meters should be readily understood. The housing, having a larger diameter than the conduit, prevents a dislodged membrane from entering the conduit where it could cause damage to the respiratory device or patient. Moreover, moisture and mucus are directed out of the housing of the present invention. In the first embodiment of the housing, although the axis of the housing is parallel to the axis of the conduit, the two axes are non-colinear. Thus, since the housing invert aligns with the conduit invert, there is no well where liquids can accumulate. In the second preferred embodiment of the housing, liquids are directed into the lower inlet/outlet port. Gas flow then forces the liquids out of the housing and into the lower conduit. Therefore, the present variable orifice flow meter includes a housing which, by preventing the accumulation of liquids, maintains measurement accuracy, improves the safety of patients and, further, minimize downtime of the respiratory system.

BRIEF DESCRIPTION OF THE DRAWINGS

FIG. 1 is a longitudinal sectional view of one prior art sensing head, or flow meter.

FIG. 2 is a transverse sectional view taken along lines 2—2 of FIG. 1, showing the orifice membrane of the prior art flow meter.

FIG. 3 is a front elevational view of a preferred embodiment of an orifice membrane, which is an improvement over the prior art, illustrating the configuration of the leaves in the obstruction diaphragm when the leaves are not deflected.

FIG. 4 is a longitudinal sectional view of one preferred embodiment of the variable area flow meter of the present invention.

FIG. 5 is a top plan view of the flow meter illustrated in FIG. 4.

FIG. 6 is a transverse elevational view of the first preferred embodiment of the flow meter illustrated in FIG. 4.

DETAILED DESCRIPTION OF THE PREFERRED EMBODIMENTS

Figure 7:
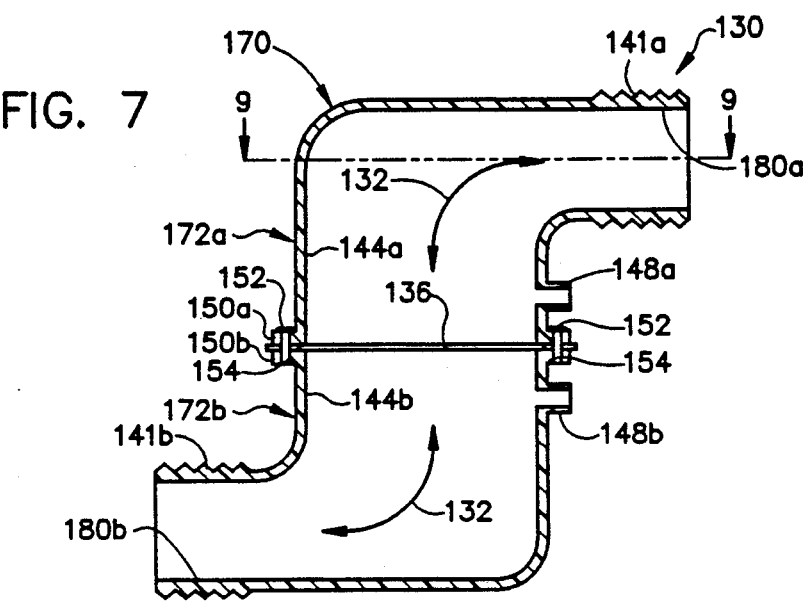
FIG. 7 is a longitudinal sectional view of another preferred embodiment of the variable area flow meter of the present invention.

Reference is now made to the drawings wherein like parts are designated with like numerals throughout.

The function and structure of the present invention may be most easily understood by comparing it to a sensing head generally indicated at 100, as illustrated in FIG. 1. The illustrated sensing head 100 is described in U.S. Pat. No. 4,083,245 to Osborn, which patent is hereby incorporated by reference herein. The sensing head 100 is disposed in a gas flow line 102. A gas flows in the direction indicated by the arrows 104 passes through the gas flow line 102 and into the sensing head 100 where it deflects a flap 106. A pair of tubes 108a, 108b on the sensing head 100 is connected to a differential pressure gauge 110. Differential pressure gauge 110 may comprise one of many conventional, commercially available pressure gauges, such as a Model NPH-8-015DH manufactured by Novasensor, Inc. of Fremont, Calif. The differential pressure gauge 110 measures the quantity of the gas flow 104 by differencing the pressure measurements at the tubes 108a and 108b.

The housing of the sensing head 100 includes a depressed well 112 surrounding the lower portion of the flap 106 and a flap ridge 114 protruding from the bottom of sensing head 100. Moisture or mucus communicated from the patient can thus accumulate in the depressed well 112 and against the flap ridge 114, achieving a depth which can contact the extended end of the flap 106. Such accumulation of liquids leads to inaccurate gas flow measurements, unsanitary conditions and frequent cleaning or replacement of the sensing head 100.

Turning now to FIG. 2, the flap 106 associated with the sensing head 100 is shown in greater detail. In particular, the flap 106 is cut out from a surrounding orifice membrane 120. Under conditions of increasing flow, the flap 106 on the orifice membrane 120 opens, and therefore lessens resistance. In this way, the turbulence of the gas flow 104 is minimized. When turbulence is reduced, the flow tends to become laminar and, under laminar flow conditions, the pressure differential around the orifice membrane 120 is substantially linear. As is well known, for many applications, the measurement of linear pressure differentials produces comparatively more accurate reading of the gas flow than does the measurement of non-linear pressure differentials.

FIG. 3 illustrates a variable area obstruction 122 which performs a function similar to the orifice membrane 120 shown in FIG. 2. The variable area obstruction 122 includes three flaps 106a, 106b, 106c. The variable area obstruction 122 is shown, and more fully discussed, in my co-pending United States patent application, entitled "VARIABLE AREA OBSTRUCTION GAS FLOW METER". It will be recognized by those skilled in the technology that the orifice membrane 120 of FIG. 2 and the variable area obstruction 122 of FIG. 3 are but two of a number of types of membranes which can be used in the flow meter housing of the present invention.

One preferred embodiment of a variable flow sensing device is presented in FIG. 4. The variable flow sensing device, generally indicated at 130, is placed in a gas flow conducting conduit (not shown) permitting a bi-directional gas, as indicated at arrows 132, to flow through the sensing device 130 as indicated by the arrows. The sensing device 130 is preferably manufactured of a lightweight material such as plastic, and it is preferably transparent so that the normal operation of the membrane can be visually monitored. The sensing device 130 comprises a housing generally indicated at 134 and a membrane 136. The membrane 136 may, for example, be of the type as illustrated previously by the variable obstruction 122 of FIG. 3 and is secured within the housing 134 by fastening means discussed below. The membrane 136 shown in FIG. 4 includes a membrane ridge 137, which is defined by a discontinuity between the main body of the membrane 136 and one or more hingably secured flaps 106.

Because the sensing device 130 to a large extent exhibits mirror-like symmetry on either side of the membrane 136, the suffixes "a" and "b" will be used with reference numerals to identify similar elements. The housing 134 comprises a pair of housing sections 138a, 138b. Each of the housing sections 138 includes a tubular inlet/outlet port 140a, 140b on one end. The inlet/outlet port 140 has a plurality of raised barbs 141a, 141b surrounding the first end of its exterior, which allow the conduit interior (not shown), generally formed from a flexible plastic, to easily engage the inlet/outlet port 140 and lock the conduit in place.

A transition section 142a, 142b formed in the housing sections 138 is located adjacent to the second end of the inlet/outlet port 140. The transition section 142 has an increasing diameter taper as it extends distally away from the inlet/outlet port 140. However, there is no taper on the invert of the transition section 142, which remains generally parallel to the central axis of the transition section 142.

A mid-section 144a, 144b of uniform diameter is formed on each housing section 138 and is located adjacent to the end of the transition section 142 having the greatest diameter. The inlet/outlet port 140, the transition section 142, and the mid-section 144 are all joined by a common invert 146a, 146b. A sensor outlet 148a, 148b is disposed on the housing opposite the invert 146 in the mid-section 144. The sensor outlet 148 is connected to one side of the differential pressure gauge 110 (FIG. 1) by the tubes 108 (FIG. 1). A connector flange 150 extends around the circumference of the distal end of the mid-section 144.

The two housing sections 138a, 138b are joined together at the adjacent connector flanges 150a, 150b by a set of screws 152. The screws 152 are secured in a set of threaded holes 154 which are formed in the connector flanges 150 so as to align when the two connector flanges 150 are joined. The screws 152 also pass through a set of holes in the membrane 136 which align with the threaded holes 154. The membrane 136 is thus held in place between the two housing sections 138a, 138b. One skilled in the art will observe that the screws 152 are but one example of a fastening means and other means of fastening such as chemical or mechanical bonding, for example, can serve the purpose of joining the housing sections 138a, 138b.

Normal operation of the sensing device 130 requires that the device 130 be placed in the horizontal position such that the sensor outlets 148 are at the top and the membrane ridge 137 is at the bottom. Because the inverts 146a, 146b of both housing sections 138a, 138b are essentially flush, moisture and mucus do not collect on the invert 146, but instead can pass through the device with minimal obstruction. In addition, the membrane ridge 137 bears a low profile, which further prevents fluids from collecting in the housing 134.

FIG. 5 is another view of the flow meter housing 134. In this view, it can be seen that the mid-sections 144 of the housing 134 are of a wider diameter than the diameter of the inlet/outlet ports 140. This is so, since the housing 134 holds the membrane 136 (FIG. 4) which is larger in diameter than the conduit (not shown) attached to the housing 134 at the inlet/outlet ports 140. In such a configuration, a detached membrane will not be passed out the conduit where it could injure the respiratory equipment or patient.

FIG. 6 illustrates the relationship among the three component sections 140, 142, 144 of the housing section generally indicated at 138. In particular, the inlet/outlet port 140 is shown to be in an eccentric relationship with the transition section 142 and the flange 150 of the mid-seCtion 144.

FIG. 7 illustrates another preferred embOdiment of the variable flow sensing device generally indicated at 130. In this embodiment, the sensing device 130 defines a "Z"-shaped housing generally indicated at 170. The "Z"-shape causes the conduit ends, between which the housing 170 is interposed, to be non-colinear in relation to one another. The housing 170 encloses a variable resistance membrane 136 such as the variable area obstruction 122 of FIG. 3. The membrane 136 is sandwiched between a pair of housing sections generally indicated at 127a, 172b. Each of the housing sections 172 has raised barbs 141a, 141b on the exterior of an upper and lower inlet/outlet port 180a, 180b similar to those found on the housing sections 138 of the embodiment of FIG. 4. The inlet/outlet port 180 is formed in the housing section 138 and is located adjacent to the mid-sections 144a, 144b. A longitudinal axis of the mid-section 144 is aligned at about a 90° angle to a longitudinal axis of the inlet/outlet port 180. A pair of substantially tubular sensor outlets 148a, 148b are formed on the exterior of the mid-sections 144 so that their axes are substantially parallel to the longitudinal axes of the inlet/outlet ports 180. The mid-sections 144a, 144b contact one another at a pair of connector flanges 150a, 150b which are secured by a set of screws 152 placed through a set of threaded holes 154.

As can be seen from FIG. 7, the "Z"-shaped housing 170 is preferably oriented so that the longitudinal axes of the inlet/outlet ports 180a, 180b are substantially horizontal. In the "Z"-shaped housing 170, liquid that enters the variable flow sensing device 130 from the upper inlet/outlet port 180a, in fluid communication with the patient (not shown) falls through the mid-sections 144 to the lower inlet/outlet port 180b as a result of gravity, thereby preventing accumulation of liquids within the housing 170. When gas travels from the upper inlet/outlet port 180a to the lower inlet/outlet port 180b any liquid is forced out of the lower inlet/outlet port 180b and into the interconnected system which may, for example, comprise a respirator (not shown).

Figure 8:
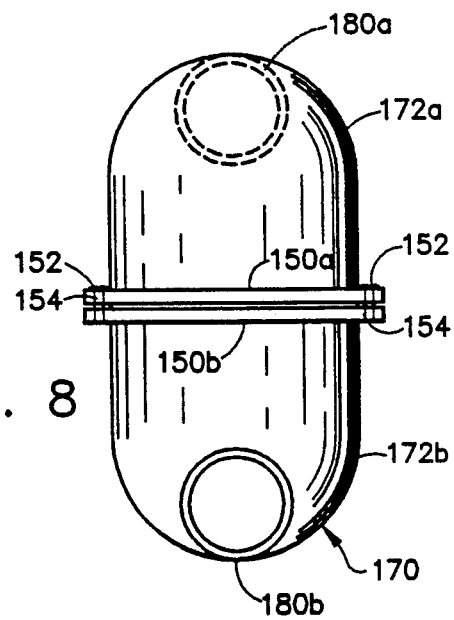
FIG. 8 is a rear elevational view of the flow meter illustrated in FIG. 7.
Figure 9:
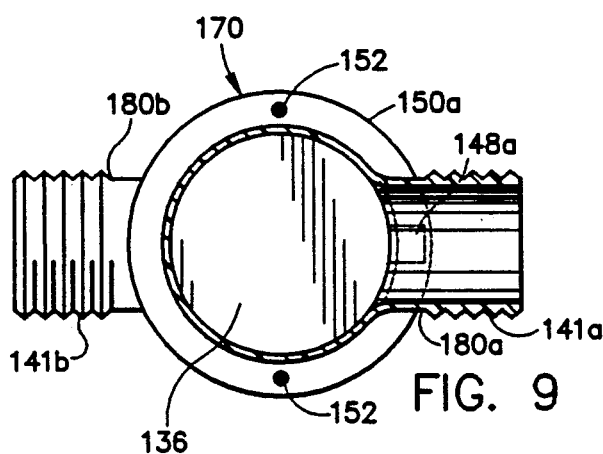
FIG. 9 is a top sectional view taken along lines 9—9 of the flow meter illustrated in FIG. 7.

By reference to FIG. 8 it is seen that the axis of the upper inlet/outlet port 180*a* is parallel to the axis of the lower inlet/outlet port 180*b*. Referring to FIG. 9, the placement of the primary surface area of the membrane 136 in the housing 170 and the cross-sectional shape of the inlet/outlet port 180 are more clearly seen.

From the foregoing description, it will be appreciated that the invention disclosed herein overcomes many longstanding problems in the related technology by (1) providing a housing for a variable flow sensing device wherein a dislodged or detached membrane is prevented from travelling down the conduit to create a blockage; (2) providing such a housing that is configured to prevent substantially all liquids that enter the conduit from accumulating within the meter, and to thereby maintain measurement accuracy; and (3) providing such a housing wherein unsanitary build-up of moisture and mucus in the flow meter is eliminated and therefore, service and downtime are minimized, and the safety of the patient is enhanced.

While the above detailed description has shown, described, and pointed out the fundamental novel features of the invention as applied to various embodiments, it will be understood that various omissions, substitutions, and changes in the form and details of the device illustrated may be made by those skilled in the art, without departing from the spirit of the invention.

What is claimed is:

1. A flow meter of the type located in a conduit and having a housing including a plurality of inlet/outlet ports,. and a plurality of differential pressure sensor ports, comprising:
    a variable orifice membrane disposed on the interior of said housing and between said differential pressure sensor ports; and
    means for preventing collection of moisture within said housing wherein said housing has a diameter greater than the diameter of said conduit and wherein said moisture preventing means is defined by providing the interior of said housing with an invert that is substantially collinear with an invert of said conduit.

2. A flow meter of the type located in a conduit and having a housing including a plurality of inlet/outlet ports, and a plurality of differential pressure sensor ports, comprising:
    a variable orifice membrane disposed on the interior of said housing and between said differential pressure sensor ports; and
    means for preventing collection of moisture within said housing wherein said housing has a diameter greater than the diameter of said conduit and wherein said moisture preventing means is defined by providing said housing with a tubular axis defined by said inlet/outlet ports which is non-collinear and parallel with an axis of said conduit so that said housing is eccentrically offset from said conduit.

3. A flow meter of the type located in a conduit and having a housing including a plurality of inlet/outlet ports, and a plurality of differential pressure sensor ports, comprising:
    a variable orifice membrane disposed on the interior of said housing and between said differential pressure sensor ports; and
    means for preventing collection of moisture within said housing wherein said housing has a diameter greater than the diameter of said conduit and wherein said inlet and outlet ports are provided on said housing such that the respective axes are relatively non-collinear but each such axis is substantially parallel to one another and the horizontal and wherein said membrane is substantially parallel to the horizontal when flow is substantially static.

4. A variable gas flow sensing device, comprising:
    a conduit having a first port at a first end thereof and a second port at a second end thereof, so that gas flows through said first and second ports and is conducted within the conduit, wherein a mid-section of the conduit is of a diameter greater than the diameter of said first and second ports and wherein said mid-section aligns eccentrically with said first and second ports, thereby forming a substantially flush surface along an interior invert of the conduit; and
    a variable orifice obstruction mounted within said mid section in said conduit between said first and second ports.

5. A sensing device as defined in claim 4, wherein said obstruction comprises a thin flexible sheet of material and said orifice is defined by a partially cut-out portion of said material creating one or more flaps hingably connected to said material capable of deflecting in either direction of flow.

6. A sensing device as defined in claim 4, additionally comprising:
    means for sensing the pressure of said gas flow positioned on said mid-section adjacent to said obstruction.

7. A sensing device as defined in claim 5, wherein said flaps are hinged at one end and are adapted to deflect in the direction of said gas flow and define said orifice as an annular-shape covered by said flaps when said gas flow is substantially quiescent.

8. A sensing device as defined in claim 7, wherein said orifice is positioned substantially flush to said invert of said mid-section to facilitate the free-flow of liquid and to prevent the accumulation thereof.

9. A sensing device as defined in claim 6, wherein said sensing means comprises an aperture through said conduit on each side of said orifice membrane, wherein said apertures are formed in said mid-section of said conduit and aligned perpendicular to an axis defined by said gas flow, thereby permitting continuous gas communication with a pressure sensing device for measuring the pressure differential across the membrane.

10. A gas flow meter, comprising:
    a housing having a set of three linear tubes joined together wherein one end of a first tube is perpendicularly joined to one end of a second tube and a third tube is perpendicularly joined to the other end of said second tube such that said first and third tubes are parallel;
    a variable orifice obstruction mounted in said second tube for blocking a portion of a gas flow communicated through said tubes, wherein the variable orifice obstruction is positioned within said second tube so as to avoid substantial influence by liquids within said second tube; and
    a pair of differential sensor ports formed on said housing so that said variable orifice obstruction is interposed therebetween.

11. A gas flow meter as defined in claim 10 wherein said obstruction is formed from a thin flexible sheet of elastic material and an orifice in said obstruction is defined by a partially cut-out portion of said obstruction creating one or more flaps hingably connected to said obstruction capable of deflecting in either direction of flow.

12. A gas flow meter as defined in claim 11, wherein said flaps are hinged at one end deflecting in the direction of said gas flow and defined said orifice as an annular-shape covered by said flaps when said gas flow is substantially quiescent.

13. A gas flow meter as defined in claim 12, wherein said orifice is positioned substantially flush to said interior surface of said second tube to facilitate the free-flow of liquid and to prevent the accumulation thereof.

14. A gas flow meter as defined in claim 10, wherein the variable orifice obstruction is mounted within the second tube and transversely secured thereto so that said obstruction extends across said second tube and the flow of gas therein.

15. A gas flow meter, comprising:
a housing having a set of three linear tubes joined together wherein one end of a first tube is perpendicularly joined to one end of a second tube and a third tube is perpendicularly joined to the other end of said second tube such said first and third tubes are parallel; and
a variable orifice obstruction mounted in said second tube for generating a gas pressure differential across said obstruction that is a function of gas flow rate through said meter, wherein the variable orifice obstruction is positioned within said second tube so as to avoid substantial influence by liquids within said second tube.

16. A gas flow meter as defined in claim 15, additionally comprising:
means for sensing the pressure of said gas flow positioned on said second tube adjacent to said obstruction.

17. A flow meter adapted for use in measuring gas flow rates, comprising:
a housing having a top and a bottom, and first and second gas inlet/outlet ports, each such port having a diameter and said first and second ports together adapted to direct gas horizontally through said housing in a flow path; and
a variable orifice membrane disposed in said flow path between said first and second ports adapted to generate a differential pressure across said membrane as a function of the flow rate of said gas through said orifice, wherein the diameters of said first and second ports are less than the diameter of said housing at the location of said membrane, and wherein the bottom of said housing inside said housing is substantially linear between said first and second ports so that liquid can move through said housing without substantial accumulation thereof at said membrane.

18. A gas flow meter, comprising:
a conduit for communicating gas therethrough;
means for preventing collection of moisture within said conduit;
a variable orifice obstruction mounted in said conduit for blocking a portion of a gas flow communicated through said conduit; and
a pair of differential sensor ports formed on said conduit so that said variable orifice obstruction is interposed therebetween, wherein the means for preventing collection of moisture comprises a midsection disposed orthogonally between the first and second ports and wherein the variable orifice obstruction is positioned transversely within said midsection so as to avoid substantial influence of liquids within said midsection on said obstruction when said midsection is oriented in a substantially vertical orientation.

* * * * *